United States Patent
Urbanczyk et al.

(10) Patent No.: US 10,551,750 B2
(45) Date of Patent: *Feb. 4, 2020

(54) METROLOGY METHOD AND APPARATUS AND ASSOCIATED COMPUTER PRODUCT

(71) Applicant: ASML Netherlands B.V., Veldhoven (NL)

(72) Inventors: Adam Jan Urbanczyk, Utrecht (NL); Hans Van Der Laan, Veldhoven (NL); Grzegorz Grzela, Utrecht (NL); Alberto Da Costa Assafrao, Veldhoven (NL); Chien-Hung Tseng, Eindhoven (NL); Jay Jianhui Chen, Fremont, CA (US)

(73) Assignee: ASML Netherlands B.V., Veldhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,055

(22) Filed: Apr. 24, 2019

(65) Prior Publication Data

US 2019/0250520 A1    Aug. 15, 2019

Related U.S. Application Data

(63) Continuation of application No. 15/874,972, filed on Jan. 19, 2018, now Pat. No. 10,310,388.

(Continued)

(51) Int. Cl.
  *G03F 7/20* (2006.01)
  *G01N 21/47* (2006.01)
  *G01N 21/956* (2006.01)

(52) U.S. Cl.
  CPC ........ *G03F 7/70625* (2013.01); *G01N 21/47* (2013.01); *G03F 7/70516* (2013.01);

(Continued)

(58) Field of Classification Search
  CPC ............ G03F 7/70525; G03F 7/70516; G03F 7/70625

(Continued)

(56) References Cited

U.S. PATENT DOCUMENTS 6,614,540 B1  9/2003  Stirton
7,262,864 B1  8/2007  Markle et al.

(Continued)

FOREIGN PATENT DOCUMENTS

EP    2503590 A1    9/2012
EP    1796136 B1    9/2015

(Continued)

OTHER PUBLICATIONS

International Search Report and Written Opinion of the International Searching Authority directed to related International Patent Application No. PCT/EP2018/050344, dated May 14, 2018; 17 pages.

(Continued)

*Primary Examiner* — Hung Nguyen
(74) *Attorney, Agent, or Firm* — Sterne, Kessler, Goldstein & Fox P.L.L.C

(57) ABSTRACT

Disclosed is a process monitoring method, and an associated metrology apparatus. The method comprises: obtaining measured target response sequence data relating to a measurement response of a target formed on a substrate by a lithographic process to measurement radiation comprising multiple measurement profiles, wherein the measured target response sequence data describes a variation of the measurement response of the target in response to variations of the measurement profiles; obtaining reference target response sequence data relating to a measurement response of the target as designed to the measurement radiation, wherein the reference target response sequence data (Continued)

describes an optimal measurement response of the target in response to designed measurement profiles without undesigned variation; comparing the measured target response sequence data and the reference target response sequence data; and determining values for variations in stack parameters of the target from the measured target response sequence data based on the comparison.

20 Claims, 6 Drawing Sheets

Related U.S. Application Data

(60) Provisional application No. 62/453,743, filed on Feb. 2, 2017.

(52) U.S. Cl.
CPC ...... *G03F 7/70525* (2013.01); *G03F 7/70633* (2013.01); *G01N 2021/95615* (2013.01)

(58) Field of Classification Search
USPC .............................................. 355/52, 53, 55
See application file for complete search history.

(56) References Cited

U.S. PATENT DOCUMENTS

| | | | |
|---|---|---|---|
| 10,094,658 B2 | 10/2018 | Takagi et al. | |
| 10,310,388 B2 * | 6/2019 | Urbanczyk | ......... G03F 7/70516 |
| 2002/0135781 A1 | 9/2002 | Singh et al. | |
| 2008/0144036 A1 | 6/2008 | Schaar et al. | |
| 2010/0175033 A1 | 7/2010 | Adel et al. | |
| 2011/0027704 A1 | 2/2011 | Cramer et al. | |
| 2011/0043791 A1 | 2/2011 | Smilde et al. | |
| 2012/0242970 A1 | 9/2012 | Smilde et al. | |
| 2014/0028993 A1 | 1/2014 | Brill | |
| 2016/0161863 A1 | 6/2016 | Den Boef et al. | |
| 2016/0282282 A1 | 9/2016 | Quintanilha et al. | |
| 2016/0299438 A1 | 10/2016 | Mos et al. | |
| 2017/0323481 A1 | 11/2017 | Tran et al. | |
| 2018/0088470 A1 | 3/2018 | Bhattacharyya et al. | |
| 2018/0217508 A1 | 8/2018 | Urbanczyk et al. | |

FOREIGN PATENT DOCUMENTS

| | | |
|---|---|---|
| WO | WO 2006/060562 A2 | 8/2006 |
| WO | WO 2009/078708 A1 | 6/2009 |
| WO | WO 2009/106279 A1 | 9/2009 |
| WO | WO 2011/012624 A1 | 2/2011 |
| WO | WO 2015/089231 A1 | 6/2015 |
| WO | WO 2016/039041 A1 | 3/2016 |
| WO | WO 2016/083076 A1 | 6/2016 |
| WO | WO 2017/147261 A1 | 8/2017 |
| WO | WO 2017/198422 A1 | 11/2017 |
| WO | WO 2018/059824 A1 | 4/2018 |

OTHER PUBLICATIONS

Choi et al., "Process Start/End Event Detection and Dynamic Time Warping Algorithms for Run-by-Run Process Fault Detection," IEEE International Symposium on Semiconductor Manufacturing, Oct. 15-17, 2007; 4 pages.

Non-Final Office Action directed to U.S. Appl. No. 15/874,972, dated Sep. 12, 2018; 10 pages.

Notice of Allowance directed to U.S. Appl. No. 15/874,972, dated Jan. 23, 2019; 5 pages.

* cited by examiner

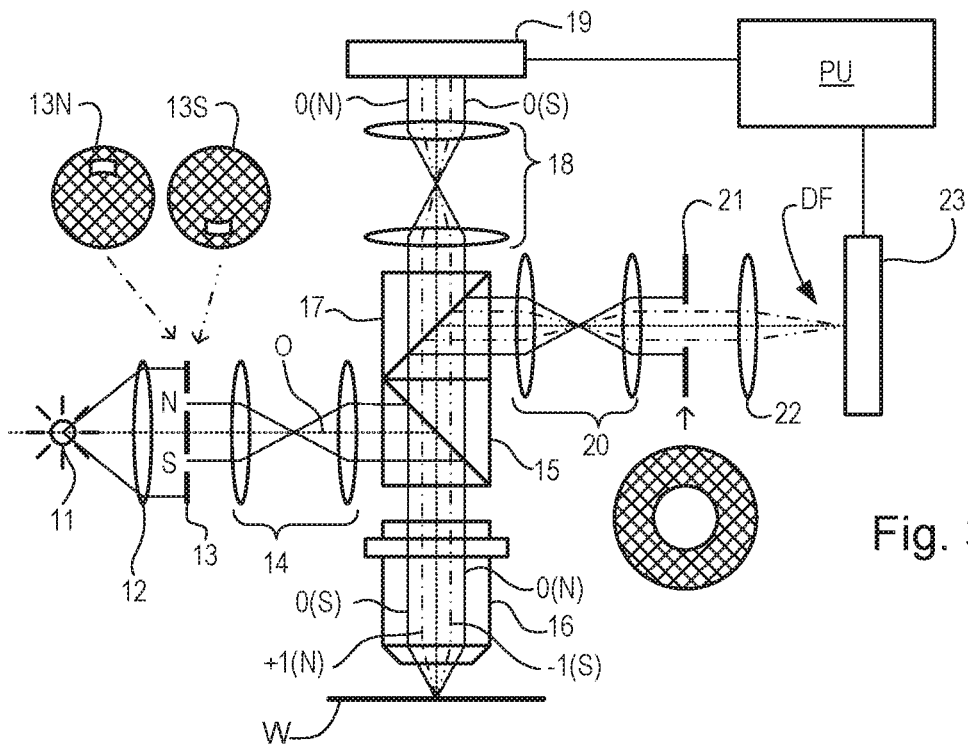
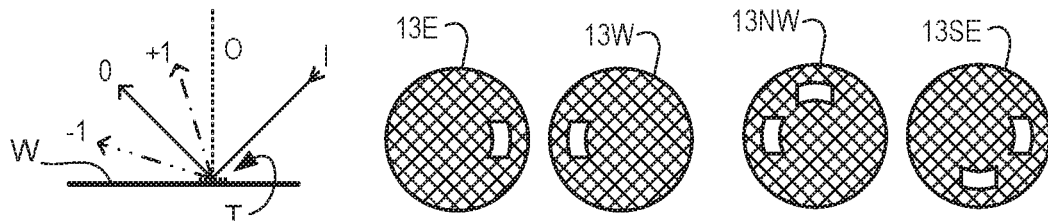
Fig. 3(b)  Fig. 3(c)  Fig. 3(d)
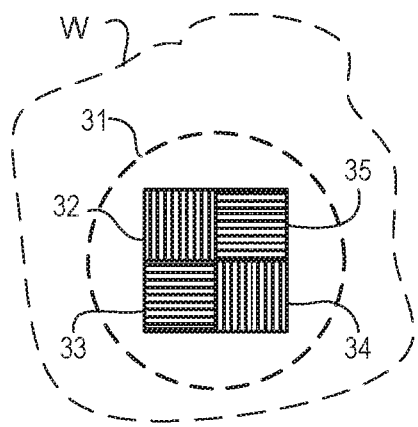
Fig. 4
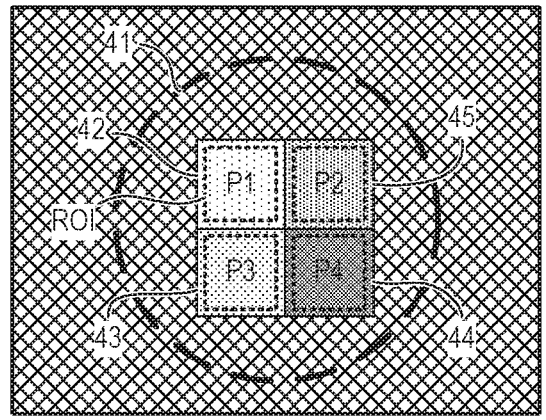
Fig. 5

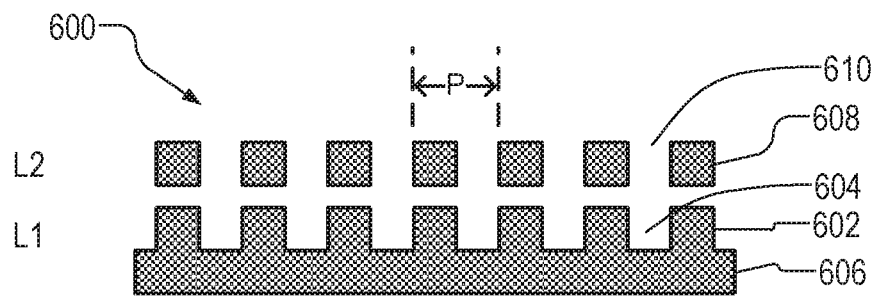
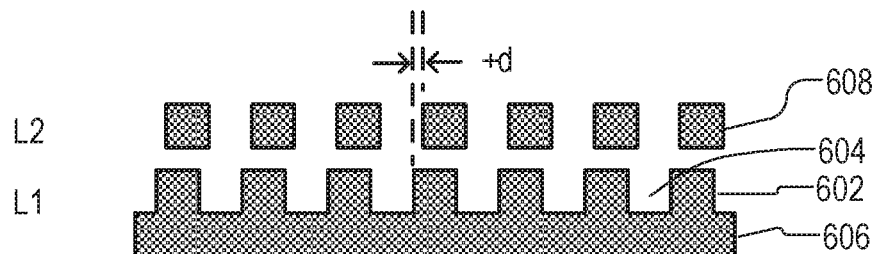
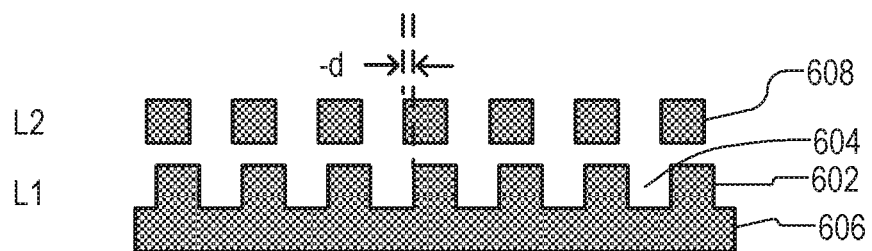
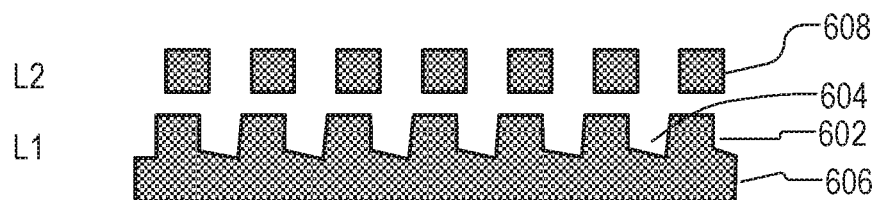
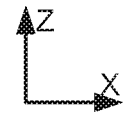

METROLOGY METHOD AND APPARATUS AND ASSOCIATED COMPUTER PRODUCT

This application is a continuation of U.S. patent application Ser. No. 15/874,972, filed Jan. 19, 2018, now U.S. Pat. No. 10,310,388, which claims benefit of U.S. Provisional Application No. 62/453,743, filed Feb. 2, 2017, and is incorporated herein in its entirety by reference.

FIELD

The present invention relates to a method, apparatus, and computer product for metrology usable, for example, in the manufacture of devices by a lithographic technique and to a method of manufacturing devices using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In a lithographic process (i.e., a process of developing a device or other structure involving lithographic exposure, which may typically include one or more associated processing steps such as development of resist, etching, etc.), it is desirable frequently to make measurements of structures created, e.g., for process control and verification. Various tools for making such measurements are known, including scanning electron microscopes, which are often used to measure critical dimension (CD), and specialized tools to measure overlay, the accuracy of alignment of two layers of a substrate. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

SUMMARY

The accuracy of target measurements depends on the combination of certain target or stack parameters and characteristics of the measurement radiation (the measurement profile) used. Therefore, target parameter and measurement profile optimization may be performed to optimize accuracy of target measurements. However, if the stack parameters of the target vary from those of targets used in the optimization step, then the measurement profile may no longer be optimal for the target during a measurement.

In addition, it may be desirable to monitor certain stack parameters of a target, for example, the heights of some or all of the layers within a stack. Measurement of layer heights is usually performed on dedicated thin film targets, separate to overlay and alignment targets. These take up additional substrate area, and their measurement takes additional measurement time.

In a first aspect of the invention there is provided a method of metrology in a metrology apparatus for monitoring a measurement process, comprising: obtaining measured target response sequence data relating to a measurement response of one or more targets formed on a substrate by a lithographic process to measurement radiation comprising a plurality of measurement profiles, wherein the measured target response sequence data describes a variation of the measurement response of the one or more targets in response to variations of the plurality of measurement profiles; obtaining reference target response sequence data relating to a measurement response of the one or more targets as designed to the measurement radiation, wherein the reference target response sequence data describes an optimal measurement response of the one or more targets in response to a designed plurality of measurement profiles without un-designed variation; comparing the measured target response sequence data and the reference target response sequence data; and determining values for variations in one or more stack parameters of the one or more targets from the measured target response sequence data based on the comparison.

In a second aspect of the invention there is provided a metrology apparatus comprising: an illumination system configured to illuminate one or more targets formed on a substrate by a lithographic process with measurement radiation comprising a plurality of measurement profiles; a detection system configured to detect scattered radiation arising from illumination of said one or more targets; and a processor operable to: derive measured target response sequence data from the detected scattered radiation, wherein the measured target response sequence data describes a variation of a measurement response of the one or more targets in response to variations of the plurality of measurement profiles, compare the measured target response sequence data to reference target response sequence data relating to a measurement response of the one or more targets as designed to the measurement radiation, wherein the reference target response sequence data describes an optimal measurement response of the one or more targets in response to a designed plurality of measurement profiles without un-designed variation, and determine values for variations in one or more stack parameters of the one or more targets from the measured target response sequence data based on the comparison.

Another aspect of the invention comprises a computer program and associated computer program carrier for performing the method of the first aspect.

BRIEF DESCRIPTION OF THE DRAWINGS

Embodiments of the invention will now be described, by way of example only, with reference to the accompanying drawings in which.

FIG. 3(a) is schematic diagram of a dark field measurement apparatus for use in measuring targets according to embodiments of the invention using a first pair of illumination apertures providing certain illumination modes;

FIG. 3(b) is a schematic detail of a diffraction spectrum of a target for a given direction of illumination;

FIG. 3(c) is a schematic illustration of a second pair of illumination apertures providing further illumination modes in using a measurement apparatus for diffraction based overlay measurements;

FIG. 3(d) is a schematic illustration of a third pair of illumination apertures combining the first and second pairs of apertures providing further illumination modes in using a measurement apparatus for diffraction based overlay measurements;

FIG. 4 depicts a form of multiple periodic structure (e.g., multiple grating) target and an outline of a measurement spot on a substrate;

FIG. 5 depicts an image of the target of FIG. 4 obtained in the apparatus of FIG. 3;

FIGS. 7(a) to 7(d) show schematic cross-sections of overlay periodic structures (e.g., gratings) having different overlay values in the region of zero;

DETAILED DESCRIPTION

Before describing embodiments in detail, it is instructive to present an example environment in which embodiments may be implemented.

Figure 1:
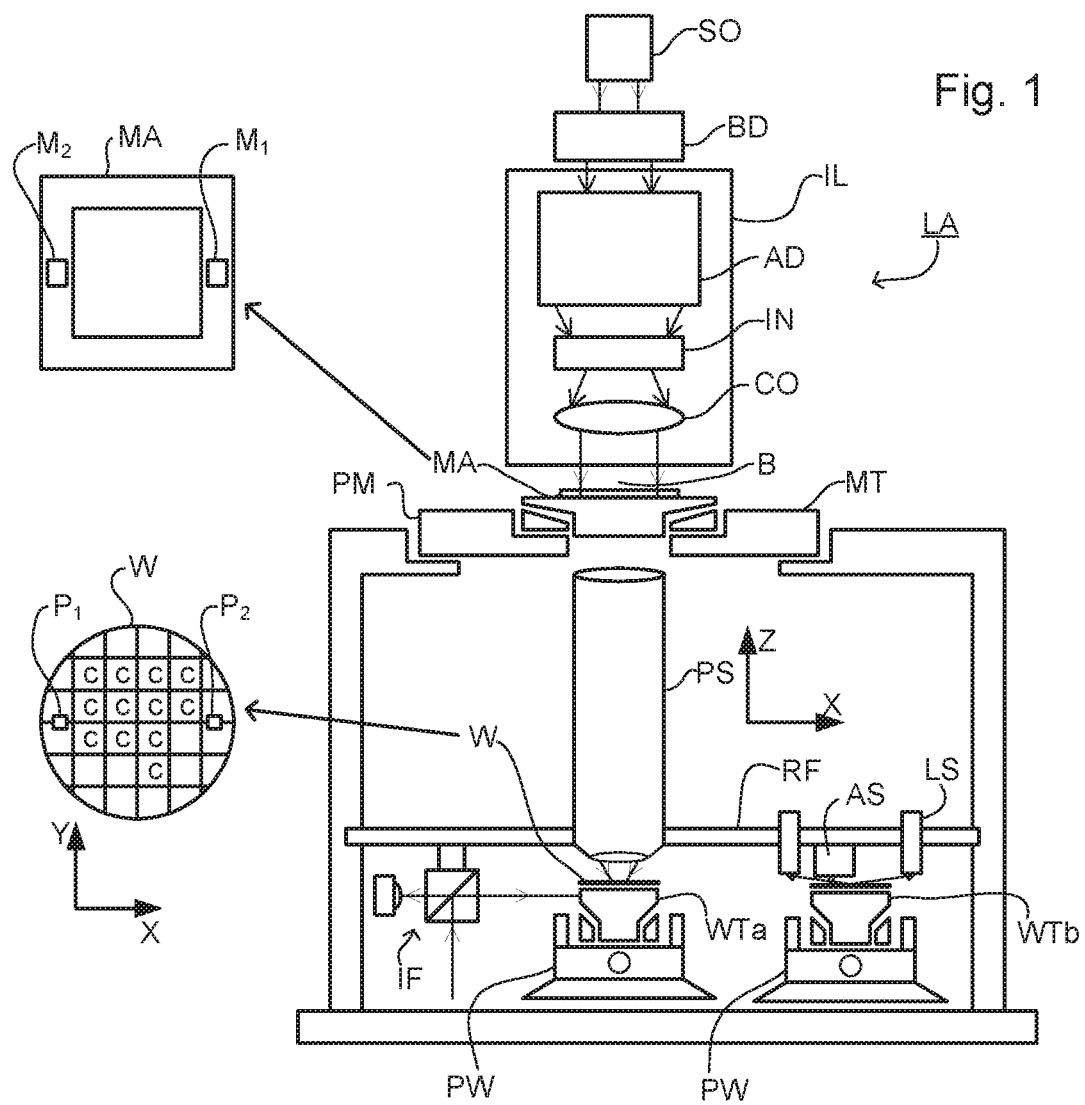
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner μW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner μW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. An embodiment of an alignment system, which can detect the alignment markers, is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
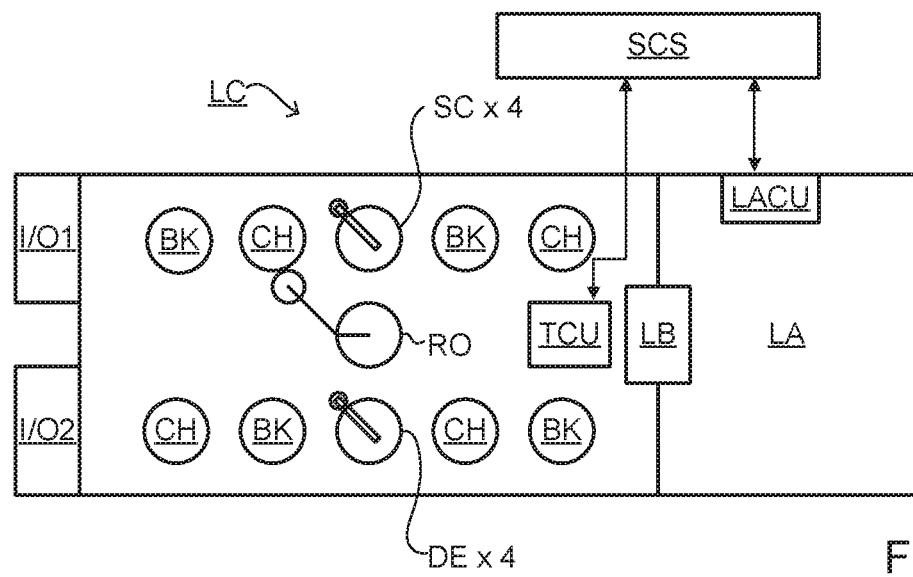
FIG. 2 depicts a lithographic cell or cluster according to an embodiment of the invention.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

A target used by a conventional scatterometer comprises a relatively large periodic structure layout (e.g., comprising one or more gratings), e.g., 40 μm by 40 μm. In that case, the measurement beam often has a spot size that is smaller than the periodic structure layout (i.e., the layout is underfilled such that one or more of the periodic structures is not completely covered by the spot). This simplifies mathematical reconstruction of the target as it can be regarded as infinite. However, for example, so the target can be positioned in among product features, rather than in the scribe lane, the size of a target has been reduced, e.g., to 20 μm by 20 μm or less, or to 10 μm by 10 μm or less. In this situation, the periodic structure layout may be made smaller than the measurement spot (i.e., the periodic structure layout is overfilled). Typically such a target is measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay (DBO or μDBO) using dark-field detection of the diffraction orders enables overlay measurements on smaller targets. These targets can be smaller than the illumination spot and may be surrounded by product structures on a substrate. In an embodiment, multiple targets can be measured in one image.

In an embodiment, the target on a substrate may comprise one or more 1-D periodic gratings, which are printed such that after development, the bars are formed of solid resist lines. In an embodiment, the target may comprise one or more 2-D periodic gratings, which are printed such that after development, the one or more gratings are formed of solid resist pillars or vias in the resist. The bars, pillars or vias may alternatively be etched into the substrate. The pattern of the grating is sensitive to chromatic aberrations in the lithographic projection apparatus, particularly the projection system PL, and illumination symmetry and the presence of such aberrations will manifest themselves in a variation in the printed grating. Accordingly, the measured data of the printed gratings can be used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other measurement processes.

A dark field metrology apparatus suitable for use in embodiments of the invention is shown in FIG. 3(a). A target T (comprising a periodic structure such as a grating) and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3(b), target T is placed with substrate W substantially normal to the optical axis O of objective lens 16. A ray of illumination I impinging on target T from an angle off the axis O gives rise to a zeroth order ray (solid line O) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through prism 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the $-1^{st}$ and the $+1^{st}$ diffraction order intensities. Comparing these intensities for a given target provides a measurement of asymmetry in the target, and asymmetry in the target can be used as an indicator of a parameter of a lithography process, e.g., overlay error. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not described in detail here.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image DF of the target formed on sensor 23 is formed from the −1 or +1 first order beam. The images captured by sensors 19 and 23 are output to image processor and controller PU, the function of which will depend on the particular type of measurements being performed. Note that the term 'image' is used here in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment of the invention, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3(c) and (d). FIG. 3(c) illustrates two further types of off-axis illumination mode. In a first illumination mode of FIG. 3(c), aperture plate 13E provides off-axis illumination from a direction designated, for the sake of description only, as 'east' relative to the 'north' previously described. In a second illumination mode of FIG. 3(c), aperture plate 13W is used to provide similar illumination, but from an opposite direction, labeled 'west'. FIG. 3(d) illustrates two further types of off-axis illumination mode. In a first illumination mode of FIG. 3(d), aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

FIG. 4 depicts an example composite metrology target formed on a substrate. The composite target comprises four periodic structures (in this case, gratings) 32, 33, 34, 35 positioned closely together. In an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs. The meaning of overlay bias will be explained below, particularly with reference to FIG. 7.

FIGS. 7(a)-(c) show schematic cross sections of overlay periodic structures (in this case gratings) of respective targets T, with different biases. These can be used on substrate W, as seen in FIGS. 3 and 4. Periodic structures with periodicity in the X direction are shown for the sake of example only. Different combinations of these periodic structures with different biases and with different orientations can be provided.

Starting with FIG. 7(a), a composite overlay target 600 formed in two layers, labeled L1 and L2, is depicted. In the bottom layer L1, a first periodic structure (in this case a grating) is formed by features (e.g., lines) 602 and spaces 604 on a substrate 606. In layer L2, a second periodic structure (in this case a grating) is formed by features (e.g., lines) 608 and spaces 610. (The cross-section is drawn such that the features 602, 608 extend into the page.) The periodic structure pattern repeats with a pitch P in both layers. Lines 602 and 608 are mentioned for the sake of example only, other types of features such as dots, blocks and via holes can be used. In the situation shown at FIG. 7(a), there is no overlay error and no bias, so that each feature 608 lies exactly over a feature 602 in the bottom periodic structure (where the measurement is "line-on-line"—in an embodiment, no overlay error may occur where each feature 608 lies exactly over a space 610 wherein the measurement is "line-on-trench").

At FIG. 7(b), the same target with a bias +d is depicted such that the features 608 of the upper periodic structure are shifted by a distance d to the right (the distance d being less than the pitch P), relative to the features 602 of the lower periodic structures. That is, features 608 and features 602 are arranged so that if they were both printed exactly at their nominal locations, features 608 would be offset relative to the features 602 by the distance d. The bias distance d might be a few nanometers in practice, for example 10 nm 20 nm, while the pitch P is for example in the range 300-1000 nm, for example 500 nm or 600 nm. At FIG. 7(c), the same target with a bias −d is depicted such that the features 608 are shifted to the left relative to the features 602. Biased targets of this type shown at FIGS. 7(a) to (c), and their use in measurement, are described in, for example, the patent application publications mentioned above.

Further, as alluded to above, while FIGS. 7(a)-(c) depicts the features 608 lying over the features 602 (with or without a small bias of +d or −d applied), which is referred to as a "line on line" target having a bias in the region of zero, a target may have a programmed bias of P/2, that is half the pitch, such that each feature 608 in the upper periodic structure lies over a space 604 in the lower periodic structure. This is referred to as a "line on trench" target. In this case, a small bias of +d or −d may also be applied. The choice between "line on line" target or a "line on trench" target depends on the application.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3(d). While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. If the periodic structures are located in product areas, product features may also be visible in the periphery of this image field. Image processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

Figure 6:
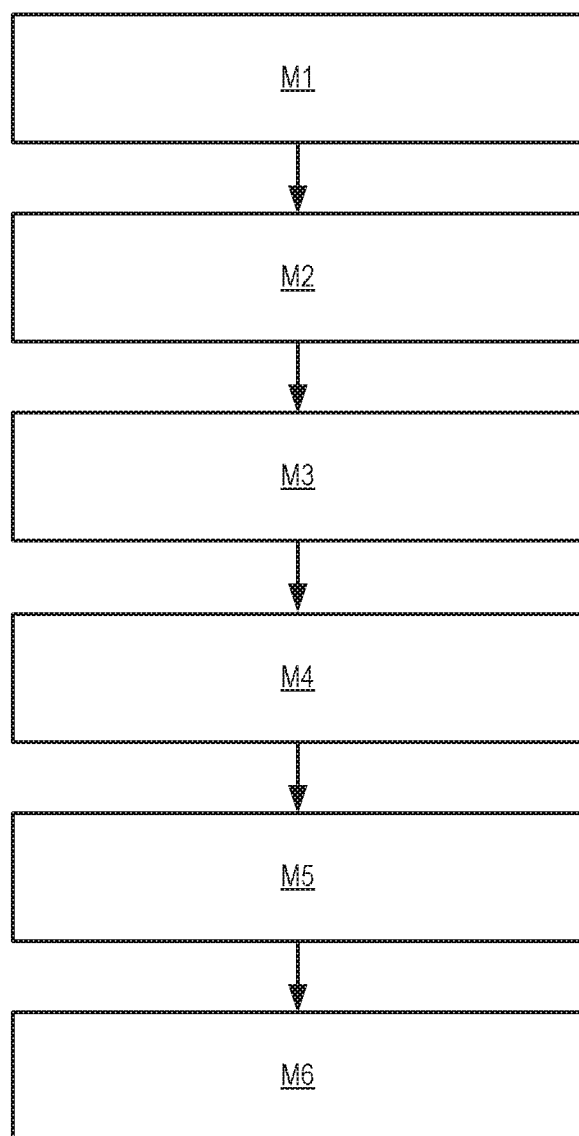
FIG. 6 is a flowchart showing the steps of an overlay measurement method using the apparatus of FIG. 3 and adaptable to embodiments of the present invention.

FIG. 6 illustrates how, using for example the method described in PCT patent application publication no. WO 2011/012624, overlay error between the two layers containing the component periodic structures 32 to 35 is measured through asymmetry of the periodic structures, as revealed by comparing their intensities in the +1 order and −1 order dark field images. At step M1, the substrate, for example a semiconductor wafer, is processed through the lithographic cell of FIG. 2 one or more times, to create a structure including the target comprising periodic structures 32-35. At M2, using the metrology apparatus of FIG. 3, an image of the periodic structures 32 to 35 is obtained using one of the first order diffracted beams (say −1). In an embodiment, a first illumination mode (e.g., the illumination mode created using aperture plate 13NW) is used. Then, whether by, for example, changing the illumination mode, or changing the imaging mode, or by rotating substrate W by 180° in the field of view of the metrology apparatus, a second image of the periodic structures using the other first order diffracted beam (+1) can be obtained (step M3). Consequently, the +1 diffracted radiation is captured in the second image. In an embodiment, the illuminated mode is changed and a second illumination mode (e.g., the illumination mode created using aperture plate 13SE) is used. In an embodiment, tool-induced artifacts like TIS (Tool Induced Shift) can be removed by doing the measurement at 0° and 180° substrate orientation.

Note that, by including only half of the first order diffracted radiation in each image, the 'images' referred to here are not conventional dark field microscopy images. The individual periodic structure features are not resolved. Each periodic structure will be represented simply by an area of a certain intensity level. In step M4, a region of interest (ROI) is identified within the image of each component periodic structure, from which intensity levels will be measured.

Having identified the region of interest P1, P2, P3, P4 for each respective individual periodic structure 32-35 and measured its intensity, the asymmetry of the periodic structure, and hence, e.g., overlay error, can then be determined. This is done by the image processor and controller PU in step M5 comparing the intensity values obtained for +1 and −1 orders for each periodic structure 32-35 to identify any difference in their intensity, i.e., an asymmetry. The term "difference" is not intended to refer only to subtraction. Differences may be calculated in ratio form. In step M6 the measured asymmetries for a number of periodic structures are used together with, if applicable, knowledge of the overlay biases of those periodic structures to calculate one or more performance parameters of the lithographic process in the vicinity of the target T. A performance parameter of interest is overlay. Other parameters of performance of the lithographic process can be calculated such as focus and/or dose. The one or more performance parameters can be fed back for improvement of the lithographic process, used to improve the measurement and calculation process of FIG. 6 itself, used to improve the design of the target T, etc.

Figure 8:
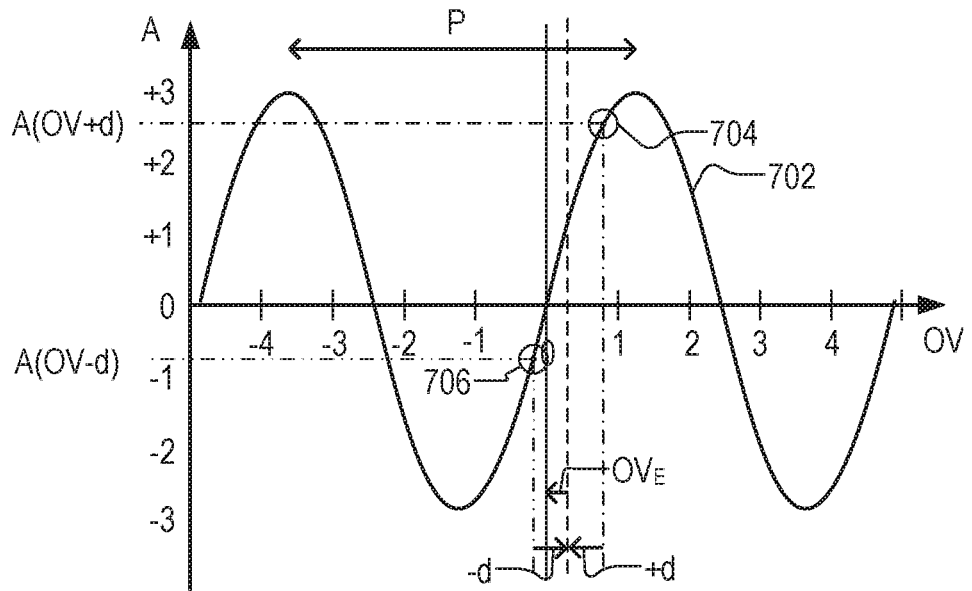
FIG. 8 illustrates principles of overlay measurement in an ideal target structure.

In an embodiment to determine overlay, FIG. 8 depicts a curve 702 that illustrates the relationship between overlay error OV and measured asymmetry A for an 'ideal' target having zero offset and no structural asymmetry within the individual periodic structures forming the overlay target. These graphs are to illustrate the principles of determining the overlay only, and in each graph, the units of measured asymmetry A and overlay error OV are arbitrary.

In the 'ideal' situation of FIGS. 7(a)-(c), the curve 702 indicates that the measured asymmetry A has a sinusoidal relationship with the overlay. The period P of the sinusoidal variation corresponds to the period (pitch) of the periodic structures, converted of course to an appropriate scale. The sinusoidal form is pure in this example, but can include harmonics in real circumstances. For the sake of simplicity, it is assumed in this example (a) that only first order diffracted radiation from the target reaches the image sensor 23 (or its equivalent in a given embodiment), and (b) that the experimental target design is such that within these first orders a pure sine-relation exists between intensity and overlay between upper and lower periodic structures results. Whether this is true in practice is a function of the optical system design, the wavelength of the illuminating radiation and the pitch P of the periodic structure, and the design and stack of the target.

As mentioned above, biased periodic structures can be used to measure overlay, rather than relying on a single measurement. This bias has a known value defined in the patterning device (e.g. a reticle) from which it was made, that serves as an on-substrate calibration of the overlay corresponding to the measured signal. In the drawing, the calculation is illustrated graphically. In steps M1-M5 of FIG. 6, asymmetry measurements $A_{+d}$ and $A_{-d}$ are obtained for component periodic structures having biases +d an −d respectively (as shown in FIGS. 7(b) and 7(c), for example). Fitting these measurements to the sinusoidal curve gives points 704 and 706 as shown. Knowing the biases, the true overlay error OV can be calculated. The pitch P of the sinusoidal curve is known from the design of the target. The vertical scale of the curve 702 is not known to start with, but is an unknown factor which we can call an overlay proportionality constant, K.

In equation terms, the relationship between overlay error $OV_E$ and intensity asymmetry A is assumed to be:

$$A_{\pm d} = K \sin(OV_E \pm d)$$

where overlay error $OV_E$ is expressed on a scale such that the target pitch P corresponds to an angle $2\pi$ radians. The term d is the grating bias of the target (or sub-target) being measured. Using two measurements of targets with different, known biases (e.g. +d and −d), the overlay error $OV_E$ can be calculated using:

$$OV_E = \operatorname{atan}\left(\frac{A_{+d} + A_{-d}}{A_{+d} - A_{-d}} \cdot \tan(d)\right)$$

where $A_{+d}$ is an intensity asymmetry measurement of the +d biased target and $A_{-d}$ is an intensity asymmetry measurement of the −d biased target.

Although these measurement techniques are fast and relatively computationally simple (once calibrated), they rely on an assumption that the overlay/lateral shift is the only cause of asymmetry. That is, it assumes an 'ideal' situation with, for example, no structural asymmetry in the target. Any structural asymmetry in the stack, such as asymmetry of features within one or both of the overlaid periodic structures, also causes an asymmetry in the $1^{st}$ orders besides the overlay/lateral shift. This structural asymmetry which is not related to the overlay clearly perturbs the measurement, giving an inaccurate result.

As an example of structural asymmetry, one or more of the periodic structures of the target may be structurally deformed. For example, one or more side walls of periodic structure features (e.g., grating lines) of the target may not be vertical as intended. As another example, one or spaces between periodic structure features (e.g., grating spaces of trenches) of a target may be larger or smaller than as intended. Further, one or more features of a periodic structure of a target (e.g., grating lines) may have a smaller or larger width than as intended. Additionally, even where a difference from intended is uniform for one or more periodic structures of the target, that difference from intended may not be the same as for one or more other periodic structures of the target. Structural asymmetry in the lower periodic structure of a composite target is a common form of structural asymmetry. It may originate, for example, in the substrate processing steps such as chemical-mechanical polishing (CMP), performed after the lower periodic structure was originally formed.

Referring to FIG. 7(d), an example of structural asymmetry of a lower periodic structure is schematically depicted. The features and spaces in the periodic structures at FIG. 7(a) to (c) are shown as perfectly square-sided, when a real feature and space would have some slope on a surface, and a certain roughness. Nevertheless they are intended to be at least symmetrical in profile. The features 602 and/or spaces 604 at FIG. 7(d) in the lower periodic structure no longer have a symmetrical form at all, but rather have become distorted by, for example, one or more processing steps. Thus, for example, a bottom surface of each space 604 has become tilted. Side wall angles of the features and spaces have become asymmetrical also. When overlay is measured by the method of FIG. 6 using only two biased periodic structures, the structural asymmetry cannot be distinguished from overlay, and overlay measurements become unreliable as a result.

It has been further discovered that, in addition to or alternatively to structural asymmetry in a target, a stack difference between adjacent periodic structures of a target or between adjacent targets may be a factor that adversely affects the accuracy of measurement, such as overlay measurement. Stack difference may be understood as an un-designed difference in physical configurations between adjacent periodic structures or targets. Stack difference causes a difference in an optical property (e.g., intensity, polarization, etc.) of measurement radiation between the adjacent periodic structures or targets that is due to a cause other than overlay error, other than intentional bias and other than structural asymmetry common to the adjacent periodic structures or targets. Stack difference includes, but is not limited to, a thickness difference between the adjacent periodic structures or targets (e.g., a difference in thickness of one or more layers such that one periodic structure or target is higher or lower than another periodic structure or target designed to be at a substantially equal level), a refractive index difference between the adjacent periodic structures or targets (e.g., a difference in refractive index of one or more layers such that the combined refractive index for the one or more layers for one periodic structure or target is different than the combined refractive index for the one or more layers for of another periodic structure or target even though designed to have a substantially equal combined refractive index), a difference in material between the adjacent periodic structures or targets (e.g., a difference in the material type, material uniformity, etc. of one or more layers such that there is a difference in material for one periodic structure or target from another periodic structure or target designed to have a substantially same material), a difference in the grating period of the structures of adjacent periodic structures or targets (e.g., a difference in the grating period for one periodic structure or target from another periodic structure or target designed to have a substantially same grating period), a difference in depth of the structures of adjacent periodic structures or targets (e.g., a difference due to etching in the depth of structures of one periodic structure or target from another periodic structure or target designed to have a substantially same depth), a difference in width (CD) of the features of adjacent periodic structures or targets (e.g., a difference in the width of features of one periodic structure or target from another periodic structure or target designed to have a substantially same width of features), etc. In some examples, the stack difference is introduced by processing steps, such as CMP, layer deposition, etching, etc. in the patterning process. In an embodiment, periodic structures or targets are adjacent if within 200 µm of each other, within 150 µm of each other, within 100 µm of each other, within 75 µm of each other, within 50 µm of each other, within 40 µm of each other, within 30 µm of each other, within 20 µm of each other, or within 10 µm of each other.

The effect of stack difference (which can be referred to as grating imbalance between gratings) on intensity asymmetry measurements $A_{+d}$, $A_{-d}$ (where the subscript indicates the target bias of the target areas corresponding to the ROIs) can be generally formulated as:

$$A_{+d} = (K + \Delta K)\sin(OV_E + d)$$

$$A_{-d} = (K - \Delta K)\sin(OV_E - d)$$

wherein $\Delta K$ represents a difference in the overlay sensitivity attributable to the stack difference. And so, the overlay error $OV_E$ (assuming it is small) can be proportional to $$\frac{\Delta K}{K} d.$$

Stack difference may be considered to be a spatial stack parameter variation, i.e., a stack parameter variation over the substrate (target-to-target). Another issue which may be encountered is stack parameter process drift, where one or more of the stack parameters of a target drift from optimal over time, due to process drift. This can be considered to be a temporal stack parameter variation.

Now, in the face of structural asymmetry, stack difference, stack parameter process drift and any other process variabilities, it is desirable to derive a combination of target layout, measurement beam wavelength, measurement beam polarization, etc. that would yield an accurate measurement of the desired process parameter (e.g., overlay) and/or that yields measurement values of the desired process parameter that is robust to process variability. Thus, it is desirable, for example, to perform measurements using a desirably optimum selection of a target-measurement parameter combination so as to obtain more accurate process parameter measurement and/or that yields measurement values of the desired process parameter that is robust to process variability. This is because the measurement accuracy and/or sensitivity of the target may vary with respect to one or more attributes of the target itself and/or one or more attributes of the measurement radiation provided onto the target; for example: the wavelength of the radiation, the polarization of the radiation, and/or the intensity distribution (i.e., angular or spatial intensity distribution) of the radiation. In an embodiment, the wavelength range of the radiation is limited to one or more wavelengths selected from a range (e.g., selected from the range of about 400 nm to 900 nm). Further, a selection of different polarizations of the radiation beam may be provided and various illumination shapes can be provided using, for example, a plurality of different apertures. As such, it is desirable to determine a measurement profile which is optimized for a particular target.

The measurement profile comprises one or more parameters of the measurement itself, the one or more parameters of the measurement itself can include one or more parameters relating to a measurement beam and/or measurement apparatus used to make the measurement. For example, if the measurement used in a substrate measurement recipe is a diffraction-based optical measurement, one or more parameters of the measurement itself may include a wavelength of measurement radiation, and/or a polarization of measurement radiation, and/or measurement radiation intensity distribution, and/or an illumination angle (e.g., incident angle, azimuth angle, etc.) relative to the substrate of measurement radiation, and/or the relative orientation relative to a pattern on the substrate of diffracted measurement radiation, and/or number of measured points or instances of the target, and/or the locations of instances of the target measured on the substrate. The one or more parameters of the measurement itself may include one or more parameters of the metrology apparatus used in the measurement, which can include detector sensitivity, numerical aperture, etc.

In this context, a pattern measured (also referred to as a "target" or "target structure") may be a pattern that is optically measured, e.g., whose diffraction is measured. The pattern measured may be a pattern specially designed or selected for measurement purposes. Multiple copies of a target may be placed on many places on a substrate. For example, a substrate measurement recipe may be used to measure overlay. In an embodiment, a substrate measurement recipe may be used to measure another process parameter (e.g., dose, focus, CD, etc.) In an embodiment, a measurement profile may be used for measuring alignment of a layer of a pattern being imaged against an existing pattern on a substrate; for example, a measurement profile may be used to align the patterning device to the substrate, by measuring a relative position of the substrate.

A number of methods have been described for evaluating and optimizing target-measurement parameter combinations. Such methods are performed in advance of production. Therefore, once optimized, the chosen target-measurement parameter combination(s) will typically be used throughout a production run, i.e., a predetermined measurement profile will be used to measure a target of a corresponding target design in accordance with a predetermined target-measurement parameter combination. However, as discussed, there may be un-designed stack parameter variation in the target, leading to stack difference between targets and/or stack parameter process drift. For example, layer thickness of one or more layers within the stack may vary over the substrate (i.e., target-to-target) and/or over time (i.e., drift). One consequence of this stack parameter variation may be that the measurement profile is no longer optimal for the target. This can result in measurements of the target being inaccurate. Stack parameter variation may also be an indication of process control issues (e.g., process drift) generally, and therefore may be a useful process monitoring metric in itself.

Figure 9:
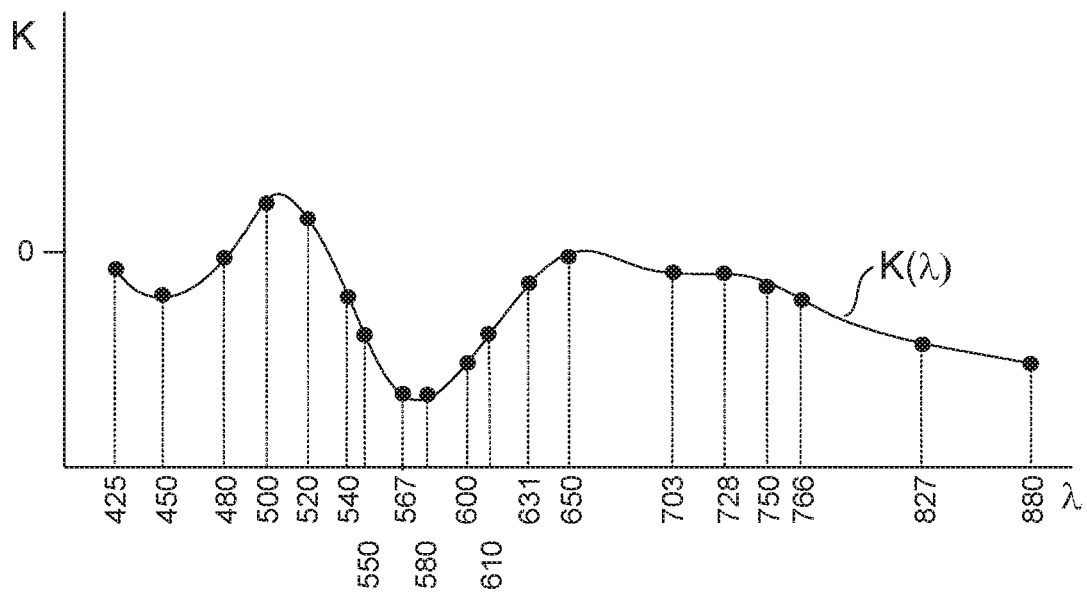
FIG. 9 is a graph of overlay sensitivity K against wavelength λ(nm) for a target, also referred to as a swing curve.

Methods for evaluating and optimizing target-measurement parameter combinations may comprise those which analyze target response sequence data describing the variation of target response with variation in the measurement profile, in particular one or more parameters of the measurement radiation such as wavelength (e.g., spectral sequence data). In an embodiment, the target response sequence data can represent an oscillatory dependence of measured data (e.g., an intensity metric obtained as field data (at an image plane) or pupil data (at pupil plane)) as a function of measurement radiation wavelength. FIG. 9 is an example graph of data for a target for measurement of an intensity metric, in this specific example overlay sensitivity K, at various wavelengths λ, for a single polarization (in this case, linear X polarization). A curve K(λ) has been fitted through the data and so this representation can be called a swing curve. As will be appreciated, a graph need not be generated as just the data can be processed. A similar graph of data can be constructed for the same target for measurement at the various wavelengths for a different single polarization (e.g., linear Y polarization). In FIG. 9, stack sensitivity and overlay sensitivity are graphed for various measurement beam wavelengths. Further, while the polarizations here is linear X polarization, it can be a different polarization (such as linear Y polarization, left-handed elliptically polarized radiation, right-handed elliptically polarized radiation, etc.)

The intensity metric may be any suitable metric derived from the detected intensities, e.g., intensity asymmetry, overlay sensitivity K or stack sensitivity (SS) (also signal contrast). Stack sensitivity can be understood as a measure of how much the intensity of the signal changes as overlay changes because of diffraction between target (e.g., grating) layers. That is, in an overlay context, it detects the contrast between upper and lower periodic structure of an overlay target and thus represents a balance between diffraction efficiencies between the upper and lower periodic structure. It is thus an example measure of sensitivity of the measurement. In an embodiment, stack sensitivity is the ratio between intensity asymmetry and average intensity. In an embodiment, stack sensitivity can be formulated as $SS=KL/I_M$, wherein L is a user defined constant (e.g., in an embodiment, the value L is 20 nm and/or the value of the bias d) and $I_M$ is the mean intensity of the measurement beam diffracted by the target.

The example of FIG. 9 shows a swing curve for overlay sensitivity K(λ) as a function of wavelength λ, where $$K(\lambda) = \frac{A(\lambda)_{+d} - A(\lambda)_{-d}}{2d * df(\lambda)}$$

$A(\lambda)_{+d}$ and $A(\lambda)_{-d}$ are the intensity asymmetry measurements corresponding to biases +d and −d respectively, as a function of wavelength and df(λ) is a dose factor as a function of wavelength. The dose factor may be any function of source intensity and measurement time. In a specific embodiment, it may comprise the product of source intensity and integration time as a function of wavelength.

It is proposed to use such swing curves to monitor measurement validity during production. Monitoring measurement validity may comprise determining whether a measurement profile remains optimal (e.g., within a threshold margin) for a target being measured. This method may comprise comparing measured target response sequence data (e.g., a measured swing curve) obtained during production to previously stored reference target response sequence data (e.g., a reference swing curve). The reference target response sequence data may have been obtained in a previous optimization stage, when determining an optimal target-measurement parameter combination, and therefore may represent the target response sequence data which would be obtained if measuring the target as designed (i.e., with little or no un-designed variation or error in stack parameters). If the comparison shows that the measured target response sequence data differs too greatly from the reference target response sequence data, then it may be decided that measurements of that target using a corresponding measurement profile in accordance with a previously determined optimized target-measurement parameter combination will be unreliable and a corrective action instigated.

It is further proposed, in an embodiment, that the swing curves can also be used to monitor stack parameters (e.g., one or more layer heights (i.e., layer thicknesses), refractive indices and/or absorptances) during production. This can provide additional process monitoring data essentially "for free", from (e.g., μDBO) measurements performed in any case to monitor overlay. The ability to measure such stack parameters can improve process control during fabrication. Presently such measurements are optically estimated using multi thin-film targets (with no gratings present). However, this requires valuable additional area on the substrate, and additional time to perform the measurements.

Figure 10:
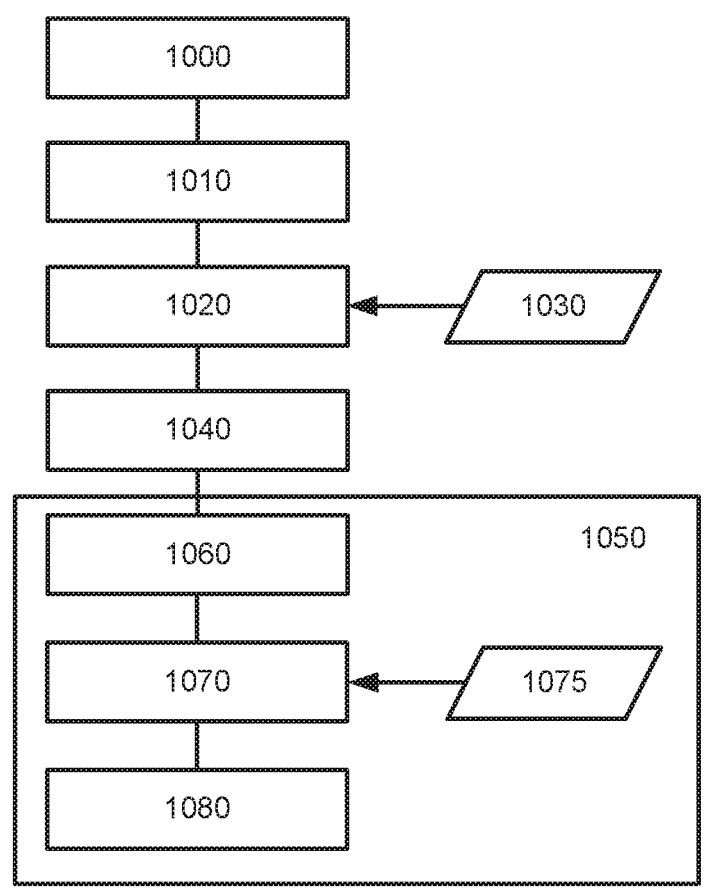
FIG. 10 is a flowchart describing a method according to a first embodiment of the invention.

FIG. 10 is a flowchart of a method according to an embodiment. At step 1000, one or more (e.g., similar) targets at one or more different locations on a substrate are measured using a plurality of different measurement profiles (e.g., over a plurality of different measurement radiation wavelengths). The targets may comprise μDBO targets. Preferably, measurement data over the different measurement profiles is obtained simultaneously for each target. For example, each measurements may be performed using broadband measurement radiation covering the different measurement profiles. The broadband radiation may comprise a continuous spectrum or a plurality of different discrete wavelengths (and/or polarizations).

At step 1010, measurement data obtained at step 1000 is used to determine measured target response sequence data (e.g., a measured swing curve comprising a spectral sequence).

At step 1020, the measured target response sequence data is compared to reference target response sequence data 1030 (e.g., a reference swing curve comprising a spectral sequence). The reference target response sequence data may have been obtained in a previous optimization step or from a previous measurement and then stored, and may comprise target response sequence data for the target as designed. The target response sequence data varies with variation in stack parameters (e.g., layer thicknesses in the stack) and therefore this comparison is indicative of the degree of difference between the actual measured target and the designed target.

In an embodiment, step 1020 may comprise using a suitable comparison algorithm to perform the comparison. An example of a suitable comparison algorithm is a dynamic time warping (DTW) algorithm, although other algorithms may also be used. The result of the comparison may be a similarity metric describing the degree of similarity between the measured target response sequence data and reference target response sequence data.

At step 1040, a validity check is performed to determine whether measurements of the target performed in accordance with a previously determined optimized target-measurement parameter combination will be valid. This may comprise comparing the similarity metric determined at step 1030 to a threshold similarity metric. If this comparison indicates that the sequences compared at step 1020 are too dissimilar, the validity check is negative (i.e., measurements will be invalid as unreliable), otherwise the validity check will be positive and measurements of the target may be continued with the previously determined optimized target-measurement parameter combination. An invalid validity check indicates that one or more of the stack parameters have changed significantly from that designed; if so, any previously performed optimization of the measurement profile based on the target as designed may be deemed invalid. The user may then be informed of this and prompted to perform a further optimization and/or target selection or other corrective action. In an embodiment, the further optimization may be performed in-line (assuming there are sufficient samples), so as to determine an updated optimal measurement profile "on the spot" based on the swing curve peaks. An invalid validity check may be an indicator of process drift in the lithography process in forming the target (and therefore in forming the product structures) and therefore may be used as a prompt for corrective action in the lithographic process.

An optional stage 1050 comprises determining values for variations in one or more of the stack parameters from the target response sequence data. This comprises using a suitable model for stack response calculation (if available) and initial stack parameter data to calculate a model which best fits the observed swing curve offset. This stage may comprise, at step 1060, constructing an error function from the measured target response sequence data and reference target response sequence data using the comparison algorithm (e.g., DTW). At step 1070, an initial stack estimate 1075 and suitable stack response model are used to simulate a swing curve for the model stack (simulated target response sequence data). The initial stack estimate 1075 may be based on the target stack as designed, i.e., the relevant stack parameters may be those as designed.

At step 1080, the error function from step 1060 is minimized using starting conditions defined at step 1070, to find the stack parameters which fit the swing curve offset. This step may comprise using a suitable optimization algorithm. An example of a suitable optimization algorithm is a Nelder-Mead Simplex algorithm. The error being minimized may comprise the difference between the measured swing curve and the simulated swing curve (i.e., the simulated target response sequence data from the model which is being minimized). Alternatively, the error being minimized may comprise the difference between the measured swing curve offset (difference between measured swing curve and reference swing curve) and a simulated swing curve offset (difference between simulated swing curve and reference swing curve). In a specific example, the minimization may comprise minimizing an L2 norm (or other suitable norm) of the comparison function (warping function) found by the comparison (e.g., DTW) algorithm.

In summary the concepts described herein enable inline monitoring of measurement validity, enabling fast flagging of suboptimal (e.g., μDBO) measurement conditions. This can be particularly useful in R&D environments where there are many process changes. The concepts also enable inline monitoring of stack parameter variation from (already routinely performed) overlay measurements, thereby reducing total metrology time. In addition, in-line profile optimization based on the swing curve peaks is possible (accepting the limited spatial sampling). If there is a significant jump or change in the swing curve shape, a new optimal measurement profile can be generated on the spot (assuming there are sufficient samples). In principle it is not necessary to stop production and execute a full holistic metrology qualification run to select new profile.

Those measurements made using the target naturally may be used in creating, for example, devices by a lithographic process. Further, besides being used to correct measurements made using the target, the measure of the asymmetric deformation of the target may be used in the (re-)design of the target (e.g., making a change to a layout of the design), may be used in the process of forming the target (e.g., making a change in material, a change in printing steps or conditions, etc.), may be used in formulation of the measurement conditions (e.g., make a change in the optical measurement formulation in terms of wavelength, polarization, illumination mode, etc. of the measurement beam), etc.

Some embodiments according to the invention are provided in below numbered clauses:

1. A process monitoring method comprising:
    obtaining measured target response sequence data relating to a measurement response of one or more targets formed on a substrate by a lithographic process to measurement radiation comprising a plurality of measurement profiles;
    obtaining reference target response sequence data relating to a measurement response of said one or more targets as designed to said measurement radiation;
    comparing said measured target response sequence data and reference target response sequence data; and
    performing a process monitoring action based on the comparison of said measured target response sequence data and reference target response sequence data.
2. A method according to clause 1, wherein said comparison step comprises determining a similarity metric relating to the similarity of the measured target response sequence data to the reference target response sequence data.
3. A method according to clause 2, wherein
    said comparison step comprises comparing said similarity metric to a threshold similarity metric; and
    said step of performing a process monitoring action comprises determining a measurement validity based on the comparing of the similarity metric to the threshold similarity metric, the measurement validity relating to a validity of measurements of said one or more targets using measurement radiation having a corresponding measurement profile in accordance with a target-measurement parameter combination.
4. A method according to clause 3, wherein said target-measurement parameter combination comprises an optimized target-measurement parameter combination determined in a previous optimization step.
5. A method according to clause 4, further comprising performing said optimization step.

6. A method according to clause 4 or 5, wherein said reference target response sequence data is determined in said optimization step.
7. A method according to any of clauses 3 to 6, wherein, where the comparison of said similarity metric to the threshold similarity metric indicates too great a dissimilarity, said measurement validity is deemed to be invalid, otherwise said measurement validity is deemed to be valid.
8. A method according to clause 7, wherein, where said measurement validity is deemed to be invalid, said step of performing a process monitoring action comprises performing an optimization update step to determine a measurement profile optimized to said one or more targets as measured.
9. A method according to clause 8, wherein, said optimization update step comprises an in-line measurement profile optimization based upon said measured target response sequence data.
10. A method according to clause 7, 8 or 9, wherein, where said measurement validity is deemed to be invalid, said step of performing a process monitoring action comprises selecting a different one or more targets for measurement.
11. A method according to any of clauses 7 to 10, wherein, where said measurement validity is deemed to be invalid, said step of performing a process monitoring action comprises performing a corrective action to said lithographic process.
12. A method according to any preceding clause, wherein the step of comparing the measured target response sequence data to the reference target response sequence data is performed using a dynamic time warping algorithm.
13. A method according to any preceding clause, wherein said measured target response sequence data and reference target response sequence data each comprise data describing the variation of the target response with measurement radiation wavelength.
14. A method according to any preceding clause, wherein the measured target response sequence data and reference target response sequence data is determined in terms of an intensity metric.
15. A method according to clause 14, wherein said intensity metric comprises an intensity asymmetry metric, derived from the intensity difference between corresponding pairs of non-zeroth diffraction orders.
16. A method according to clause 15, wherein said intensity asymmetry metric comprises overlay sensitivity, said overlay sensitivity comprising a proportionality constant in a relationship between a function of an overlay offset between periodic structures of a target and said intensity difference.
17. A method according to clause 15, wherein said intensity asymmetry metric comprises stack sensitivity, wherein stack sensitivity is the ratio of the overlay sensitivity to a measured average intensity, said overlay sensitivity comprising a proportionality constant in a relationship between a function of an overlay offset between periodic structures of a target and said intensity difference.
18. A method according to any preceding clause, further comprising determining values for one or more stack parameters of said one or more targets formed on the substrate from said measured target response sequence data.
19. A method according to clause 18, wherein said determining values for one or more stack parameters comprises:
    determining a suitable target model parameterized at least in part by said stack parameters;
    performing a simulated measurement of said target model to obtain a simulated target response sequence data; and
    minimizing the difference between said simulated target response sequence data and said measured target response sequence data.
20. A method according to clause 19, wherein said minimization step comprises devising an error function for minimizing the difference between said simulated target response sequence data and said measured target response sequence data.
21. A method according to any of clauses 18 to 20, wherein said one or more stack parameters comprise at least one layer height of a layer comprised in the target.
22. A method according to any of clauses 18 to 20, wherein said one or more stack parameters comprise a plurality of layer heights of different layers comprised in the target.
23. A method according to any preceding clause, wherein said measured target response sequence data relates to one or more dark-field measurements of said one or more targets wherein said at least one corresponding pair of non-zeroth diffraction orders is detected in an image plane.
24. A method according to any preceding clause, wherein each of said one or more targets each comprises at least two sub-targets, each sub-target having a different imposed overlay bias.
25. A method according to any preceding clause, comprising performing a measurement of said one or more targets to obtain said measured target response sequence data.
26. A metrology apparatus comprising:
    an illumination system configured to illuminate one or more targets formed on a substrate by a lithographic process with measurement radiation comprising a plurality of measurement profiles;
    a detection system configured to detect scattered radiation arising from illumination of said one or more targets; and
    a processor operable to:
      derive measured target response sequence data from the detected scattered radiation; and
      compare said measured target response sequence data to reference target response sequence data relating to a measurement response of said one or more targets as designed to said measurement radiation.
27. A metrology apparatus according to clause 26, being operable to perform a process monitoring action based on the comparison of said measured target response sequence data and reference target response sequence data.
28. A metrology apparatus according to clause 27, wherein said processor is operable to perform said comparison by determining a similarity metric relating to the similarity of the measured target response sequence data to the reference target response sequence data.
29. A metrology apparatus according to clause 28, wherein said processor is operable to:
    perform said comparison by comparing said similarity metric to a threshold similarity metric; and
    determine a measurement validity based on the comparison of the similarity metric to the threshold similarity metric, the measurement validity relating to a validity of measurements of said one or more targets using measurement radiation having a corresponding measurement profile in accordance with a target-measurement parameter combination.

30. A metrology apparatus according to clause 29, wherein said target-measurement parameter combination comprises a predetermined optimized target-measurement parameter combination.
31. A metrology apparatus according to clause 30, being operable to optimize the target-measurement parameter combination.
32. A metrology apparatus according to clause 29, 30 or 31, wherein said processor is operable, where the comparison of said similarity metric to the threshold similarity metric indicates too great a dissimilarity, to deem said measurement validity to be invalid, otherwise to deem said measurement validity to be valid.
33. A metrology apparatus according to clause 32, wherein, where said measurement validity is deemed to be invalid, said processor is operable to perform an optimization update to determine a measurement profile optimized to said one or more targets as measured.
34. A metrology apparatus according to clause 33, wherein, said optimization update comprises an in-line measurement profile optimization based upon said measured target response sequence data.
35. A metrology apparatus according to clause 32, 33 or 34, wherein, where said measurement validity is deemed to be invalid, said processor is operable to select a different one or more targets for measurement.
36. A metrology apparatus according to any of clauses 32 to 35, wherein, where said measurement validity is deemed to be invalid, said processor is operable to determine a correction for said lithographic process.
37. A metrology apparatus according to any of clauses 26 to 36, wherein the step of comparing the measured target response sequence data to the reference target response sequence data is performed using a dynamic time warping algorithm.
38. A metrology apparatus according to any of clauses 26 to 37, wherein said measured target response sequence data and reference target response sequence data each comprise data describing the variation of the target response with measurement radiation wavelength.
39. A metrology apparatus according to any of clauses 26 to 38, wherein the processor is operable to determine the measured target response sequence data and reference target response sequence data in terms of an intensity metric.
40. A metrology apparatus according to clause 39, wherein said intensity metric comprises an intensity asymmetry metric, and the processor is operable to derive the intensity asymmetry metric from the intensity difference between corresponding pairs of non-zeroth diffraction orders.
41. A metrology apparatus according to clause 40, wherein said intensity asymmetry metric comprises overlay sensitivity, said overlay sensitivity comprising a proportionality constant in a relationship between a function of an overlay offset between periodic structures of a target and said intensity difference.
42. A metrology apparatus according to clause 40, wherein said intensity asymmetry metric comprises stack sensitivity, wherein stack sensitivity is the ratio of the overlay sensitivity to a measured average intensity, said overlay sensitivity comprising a proportionality constant in a relationship between a function of an overlay offset between periodic structures of a target and said intensity difference.
43. A metrology apparatus according to any of clauses 26 to 42, wherein the processor is operable to determine values for one or more stack parameters of said one or more targets formed on the substrate from said measured target response sequence data.
44. A metrology apparatus according to clause 43, wherein the processor is operable to:
    determine a suitable target model parameterized at least in part by said stack parameters;
    perform a simulated measurement of said target model to obtain a simulated target response sequence data; and
    minimize the difference between said simulated target response sequence data and said measured target response sequence data to determine said one or more stack parameters.
45. A metrology apparatus according to clause 44, wherein the processor is operable to devise an error function for minimizing the difference between said simulated target response sequence data and said measured target response sequence data.
46. A metrology apparatus according to any of clauses 43 to 45, wherein said one or more stack parameters comprise at least one layer height of a layer comprised in the target.
47. A metrology apparatus according to any of clauses 43 to 45, wherein said one or more stack parameters comprise a plurality of layer heights of different layers comprised in the target.
48. A metrology apparatus according to any of clauses 26 to 47, being operable to perform one or more dark-field measurements of said one or more targets wherein said scattered radiation comprises at least one corresponding pair of non-zeroth diffraction orders which is detected by the detection system in an image plane.
49. A metrology apparatus according to any of clauses 26 to 48, wherein each of said one or more targets each comprises at least two sub-targets, each sub-target having a different imposed overlay bias.
50. A computer program comprising program instructions operable to perform the method according to any of clauses 1 to 25 when run on a suitable apparatus.
51. A non-transient computer program carrier comprising the computer program of clause 50.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of metrology in a metrology apparatus for monitoring a measurement process, comprising:
    obtaining measured target response sequence data relating to a measurement response of one or more targets formed on a substrate by a lithographic process to measurement radiation comprising a plurality of measurement profiles, wherein the measured target response sequence data describes a variation of the measurement response of the one or more targets in response to variations of the plurality of measurement profiles;
    obtaining reference target response sequence data relating to a measurement response of the one or more targets as designed to the measurement radiation, wherein the reference target response sequence data describes an optimal measurement response of the one or more targets in response to a designed plurality of measurement profiles without un-designed variation;
    comparing the measured target response sequence data and the reference target response sequence data; and
    determining values for variations in one or more stack parameters of the one or more targets from the measured target response sequence data based on the comparison.

2. The method of claim 1, wherein determining the values for variations in the one or more stack parameters comprises:
    constructing an error function from the measured target response sequence data and reference target response sequence data based on the comparison;
    generating simulated target response sequence data;
    minimizing the error function using the simulated target response sequence data as an initial condition to determine the values for variations in the one or more stack parameters.

3. The method of claim 2, wherein generating the simulated target response sequence data comprises:
    determining a target stack response model parameterized at least in part by the stack parameters; and
    performing a simulated measurement of the target stack response model to obtain the simulated target response sequence data.

4. The method of claim 2, wherein minimizing the error function comprises:
    minimizing a difference between the simulated target response sequence data and the measured target response sequence data.

5. The method of claim 2, wherein minimizing the error function comprises:
    calculating a first difference between the measured target response sequence data and the reference target response sequence data;
    calculating a second difference between the simulated target response sequence data and the reference target response sequence data; and
    minimizing a third difference between first difference and the second difference.

6. The method of claim 2, wherein minimizing the error function comprises using a Nelder-Mead Simplex algorithm to minimize the error function.

7. The method of claim 2, wherein comparing the measured target response sequence data and the reference target response sequence data comprises:
    performing a dynamic time warping algorithm to determining the warping function to describe a similarity of the measured target response sequence data to the reference target response sequence data.

8. The method of claim 7, wherein minimizing the error function comprises minimizing a norm of the warping function.

9. The method of claim 1, wherein the variations in one or more stack parameters indicate spatial variations over the substrate.

10. The method of claim 8, wherein the one or more stack parameters comprise at least one layer height of a layer comprised in the target.

11. The method of claim 8, wherein the one or more stack parameters comprise a plurality of layer heights of different layers comprised in the target.

12. The method of claim 1, wherein the measured target response sequence data relates to one or more dark-field measurements of the one or more targets.

13. The method of claim 1, wherein each of the one or more targets comprises at least two sub-targets, each sub-target having a different imposed overlay bias.

14. The method of claim 1, wherein the variations of the plurality of measurement profiles comprises variations of an intensity distribution of the measurement radiation of the plurality of measurement profiles.

15. The method of claim 1, wherein the variations of the plurality of measurement profiles comprises variations of a wavelength of the measurement radiation of the plurality of measurement profiles.

16. The method of claim 1, wherein the variations of the plurality of measurement profiles comprises variations of a polarization of the measurement radiation of the plurality of measurement profiles.

17. The method of claim 1, wherein the variations of the plurality of measurement profiles comprises variations of an illumination angle relative to the substrate of the measurement radiation of the plurality of measurement profiles.

18. The method of claim 1, wherein the measured target response sequence data and the reference target response sequence data each comprise an intensity metric as a function of measurement radiation wavelength, the intensity metric describing an intensity difference between a pair of non-zeroth diffraction orders.

19. A metrology apparatus comprising:
    an illumination system configured to illuminate one or more targets formed on a substrate by a lithographic process with measurement radiation comprising a plurality of measurement profiles;
    a detection system configured to detect scattered radiation arising from illumination of said one or more targets; and
    a processor operable to:

derive measured target response sequence data from the detected scattered radiation, wherein the measured target response sequence data describes a variation of a measurement response of the one or more targets in response to variations of the plurality of measurement profiles, compare the measured target response sequence data to reference target response sequence data relating to a measurement response of the one or more targets as designed to the measurement radiation, wherein the reference target response sequence data describes an optimal measurement response of the one or more targets in response to a designed plurality of measurement profiles without un-designed variation, and determine values for variations in one or more stack parameters of the one or more targets from the measured target response sequence data based on the comparison.

20. A non-transitory computer program product comprising machine readable instructions which, when run on a suitable processor of a lithographic system, cause the processor to perform a method of metrology in a metrology apparatus for monitoring a measurement process, the method comprising:

obtaining measured target response sequence data relating to a measurement response of one or more targets formed on a substrate by a lithographic process to measurement radiation comprising a plurality of measurement profiles, wherein the measured target response sequence data describes a variation of the measurement response of the one or more targets in response to variations of the plurality of measurement profiles;

obtaining reference target response sequence data relating to a measurement response of the one or more targets as designed to the measurement radiation, wherein the reference target response sequence data describes an optimal measurement response of the one or more targets in response to a designed plurality of measurement profiles without un-designed variation;

comparing the measured target response sequence data and the reference target response sequence data; and determining values for variations in one or more stack parameters of the one or more targets from the measured target response sequence data based on the comparison.

* * * * *

UNITED STATES PATENT AND TRADEMARK OFFICE
CERTIFICATE OF CORRECTION

PATENT NO. : 10,551,750 B2
APPLICATION NO. : 16/393055
DATED : February 4, 2020
INVENTOR(S) : Urbanczyk et al.

Page 1 of 1

It is certified that error appears in the above-identified patent and that said Letters Patent is hereby corrected as shown below:

In the Claims

Column 26, Line 7, please replace "first difference" with --the first difference--.

Signed and Sealed this
Fifth Day of May, 2020

Andrei Iancu
*Director of the United States Patent and Trademark Office*